United States Patent [19]

Good et al.

[11] Patent Number: 5,334,851
[45] Date of Patent: * Aug. 2, 1994

[54] COMPUTED RADIOGRAPHY PATIENT IDENTIFICATION SYSTEM

[75] Inventors: Walter F. Good; David Gur, both of Pittsburgh, Pa.; James F. Owen, Rochester, N.Y.; Bruce R. Whiting, Pittsford, N.Y.; David L. Modney, Fairport, N.Y.; Richard Weil, Pittsford, N.Y.

[73] Assignees: Eastman Kodak Company, Rochester, N.Y.; University of Pittsburgh, Pittsburgh, Pa.

[*] Notice: The portion of the term of this patent subsequent to Nov. 23, 2010 has been disclaimed.

[21] Appl. No.: 963,036

[22] Filed: Oct. 19, 1992

Related U.S. Application Data

[63] Continuation of Ser. No. 656,900, Feb. 15, 1991, abandoned.

[51] Int. Cl.⁵ .............................................. G01N 23/04
[52] U.S. Cl. .................................... 250/582; 250/584; 378/116
[58] Field of Search ........................... 378/165, 116; 250/327.2, 484.1, 581–587; 364/413.13

[56] References Cited

U.S. PATENT DOCUMENTS

| | | | |
|---|---|---|---|
| Re. 31,847 | 3/1985 | Luckey | 250/327.2 |
| 4,160,906 | 7/1979 | Daniels et al. | 378/116 |
| 4,641,242 | 2/1987 | Kimura | 250/337 |
| 4,739,480 | 4/1988 | Oono et al. | 378/165 |
| 4,857,713 | 8/1989 | Brown | 235/472 |
| 4,885,468 | 12/1989 | Shimura | 378/198 |
| 4,984,260 | 1/1991 | Koyama | 378/172 |
| 5,014,045 | 5/1991 | Shimura et al. | 250/584 |

Primary Examiner—Carolyn E. Fields
Attorney, Agent, or Firm—William F. Noval

[57] ABSTRACT

A computed radiography patient identification system which matches a patient with an X-ray image of the patient stored in a stimulable storage phosphor. The system includes a patient identifying bar code uniquely identifying a patient; a stimulable storage phosphor identifying bar code uniquely identifying a stimulable storage phosphor and a portable bar code scanner. The bar code scanner is used to scan the patient bar code and the storage phosphor bar code when a patient is exposed to an X-ray which is stored on the stimulable storage phosphor. Preferably, a mobile X-ray source has an associated set of bar codes identifying X-ray examination types (chest, head, limb, etc.) and/or X-ray exposure conditions. The bar code scanner scans the examination type bar code at the time the X-ray of the patient is taken. The system includes a storage phosphor reader for converting an X-ray image stored in a storage phosphor into an X-ray image signal. The bar code identification of such stimulable phosphor is also read out. The storage phosphor reader receives from the portable bar code reader, information relating to patient identification, storage phosphor identification and examination type and matches the patient identification and examination type with the X-ray image signal.

5 Claims, 4 Drawing Sheets

COMPUTED RADIOGRAPHY PATIENT IDENTIFICATION SYSTEM

This is a Continuation of application Ser. No. 656,900, filed Feb. 15, 1991 now abandoned.

BACKGROUND OF THE INVENTION

Technical Field

This invention relates in general to computed radiography in which an X-ray image of a patient is stored in a photostimulable storage phosphor. More particularly, the present invention relates to a system for matching patient identification with the patient's X-ray image stored in a storage phosphor.

Background Art

In conventional radiography, a patient is exposed to X-rays to produce an X-ray image on a photosensitive film. The film is developed and viewed by a radiologist who makes a diagnosis of the patient. A significant problem in medical imaging systems involves matching the patient name with the image recorded. In current film based radiography systems, an identification camera is used to print the patient name, date and other information on the film after it has been exposed and prior to processing. Alternatively, pressure sensitive labels with patient information may be applied after the film has been processed.

Because of the inherent disadvantages of film radiography in the acquisition, storage and transmission of X-ray images, there has been proposed a computed radiography system. Temporary X-ray images stored in a storage phosphor are converted into an X-ray image digital signal which can be stored, processed and transmitted. As described in U.S. Pat. No. 31,847, reissued Mar. 12, 1985 to Luckey, a photostimulable phosphor sheet is exposed to an image-wise pattern of short wavelength radiation, such as X-ray radiation, to record a latent image pattern in the photostimulable phosphor sheet. The latent image is read out by stimulating the phosphor with a relatively long wavelength stimulating radiation, such as red or infrared light. Upon stimulation, the stimulable phosphor releases emitted radiation of an intermediate wavelength, such as blue or violet light, in proportion to the quantity of X-ray radiation that was received. An X-ray image signal is produced by scanning the stimulable phosphor sheet in a raster pattern by means of a beam of laser light deflected by an oscillating or rotating scanning mirror. The emitted radiation is sensed by a photodetector to produce an electrical X-ray image signal. This signal may then be stored, transmitted, or displayed on a monitor or reproduced as an X-ray film.

As with film-based radiography, computed radiography requires the matching of an X-ray image with the patient. In situations where many X-rays are taken, such as in an intensive care unit of a large hospital, the management of identification of X-rays with patients can be monumental. In order to process an X-ray image signal as a function of X-ray exposure conditions, it is also desirable to match X-ray exposure conditions and other patient identification data with the X-ray image signal. Such matching results in proper diagnosis by a diagnostician (such as a radiologist) who views the X-ray image on a monitor or X-ray film reproduction. In a known computed radiography system, patient information is entered into a workstation and is transferred to a magnetic card. After an X-ray exposure on a storage phosphor is made, a technician places the cassette containing the exposed storage phosphor into a reader and dumps the patient data into the reader by swiping the magnetic card through an associated magnetic card reader. Many problems exist with this system, including double entry of patient data, which is typically entered into a computer at the time a patient is admitted into a hospital. Moreover, the specific ordering of computed radiography cassettes and patient data must be maintained.

SUMMARY OF THE INVENTION

According to the present invention, there is provided a computed radiography identification system which obviates the disadvantages of known film-based radiography and computed radiography identification systems. According to an aspect of the present invention, a storage phosphor is provided with a storage phosphor identifying bar code which uniquely identifies the storage phosphor. A patient identifying bar code uniquely identifies each patient. Preferably, a mobile X-ray unit has an associated set of bar codes identifying X-ray examination types and/or x-ray exposure conditions. A portable bar code scanner reads the storage phosphor identifying bar code, the patient identifying bar code and the X-ray exam type bar code at the time of an X-ray of the patient. This information is stored in memory in the bar code scanner. A computed radiography storage phosphor reader reads an exposed storage phosphor to convert the stored X-ray image into an X--ray image signal. The patient ID, storage phosphor ID and X-ray exam type information is loaded into the storage phosphor reader where it is matched with the proper X-ray image signal.

BRIEF DESCRIPTION OF THE DRAWINGS

In the detailed description of the invention presented below, reference is made to the accompanying drawings in which like elements are numbered with like numbers.

DESCRIPTION OF THE PREFERRED EMBODIMENT

Figure 1:
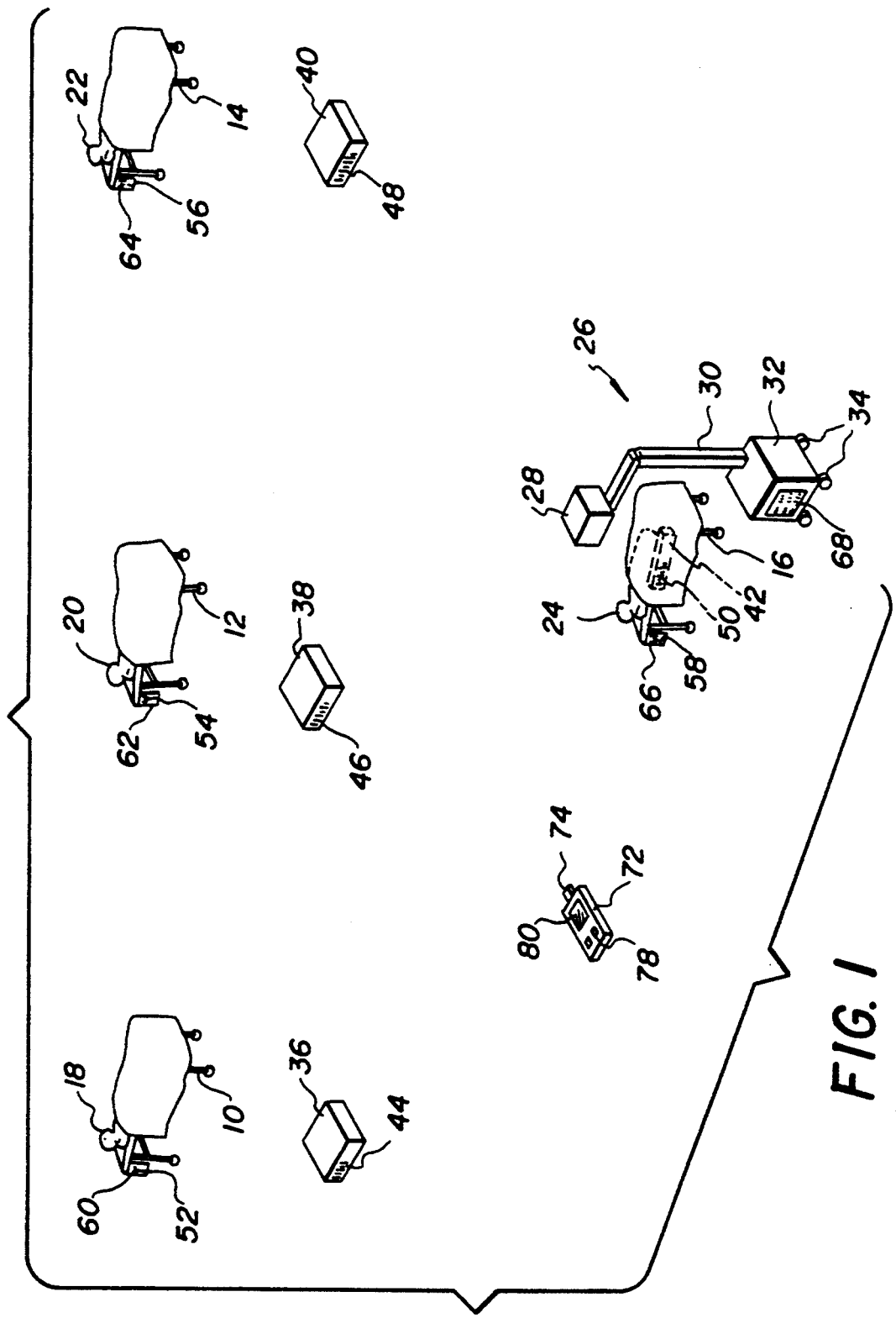
FIG. 1 is a perspective view of a medical care facility incorporating an embodiment of the present invention.

Referring now to FIG. 1, there will be described an embodiment of the present invention as used in a multi-bed medical care facility such as the intensive care unit of a hospital. As shown, the medical care facility includes a plurality of beds 10, 12, 14, and 16 having respective patients 18, 20, 22, and 24 who require medical treatment. A mobile X-ray unit 26 has an X--ray source 28 mounted on a moveable arm 30 supported by cabinet 32. Cabinet 32 includes controls and power supply for X-ray source 28. Wheels 34 on cabinet 32 facilitate moving unit 26 from bed to bed.

According to the present invention, an X-ray image of a body part of a patient is produced in a stimulable storage phosphor contained in a cassette. Thus, storage phosphor cassettes 36, 38, 40, and 42 are provided for patients 18, 20, 22, and 24, respectively. Cassettes 36, 38, 40, and 42 have storage phosphor identifying bar codes 44, 46, 48 and 50 which uniquely identify each storage phosphor.

Figure 2:
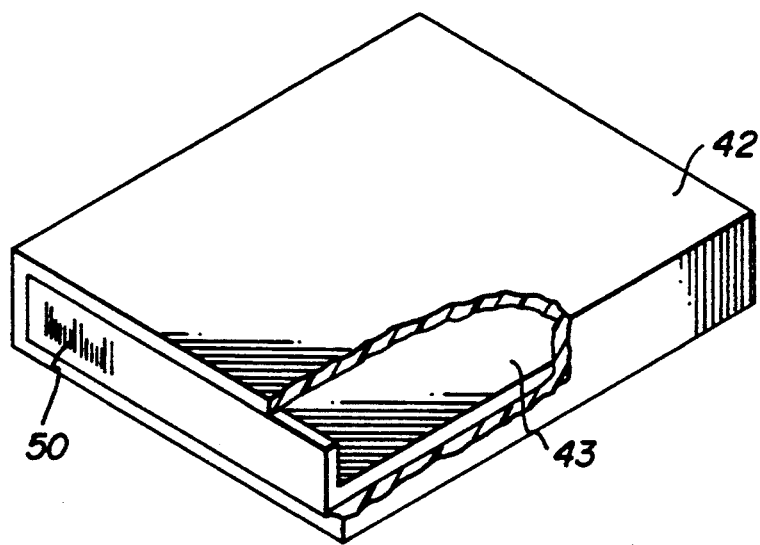
FIG. 2 is a partially broken away perspective view of a storage phosphor cassette shown in FIG. 1.

As shown in FIG. 2, storage phosphor cassette 42 has a removable storage phosphor plate 43 with bar code 50. An exemplary storage phosphor cassette is disclosed in commonly assigned, copending U.S. application Ser. No. 617,121 now U.S. Pat. No. 5,065,866.

Figure 3:
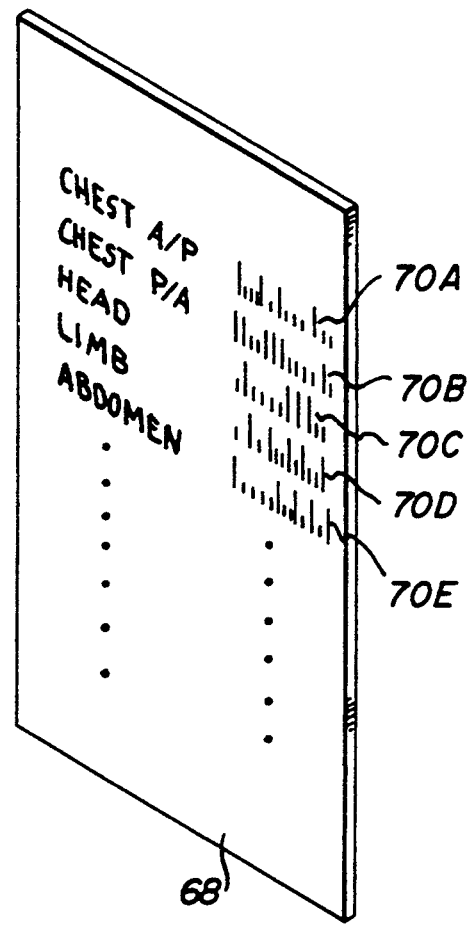
FIG. 3 is a diagrammatic view of an X-ray exam type chart shown in FIG. 1.
Figure 4:
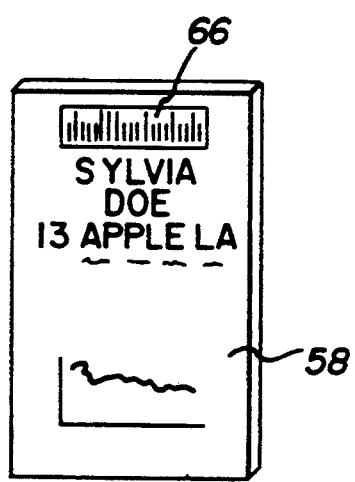
FIG. 4 is a diagrammatic view of a patient ID chart shown in FIG. 1.

Each patient 18, 20, 22, and 24 is provided a unique patient identifying bar code 52, 54, 56, and 58 on respective patient charts 60, 62, 64, and 66. X-ray unit 26 has associated with it a chart 68 having a list of X-ray exam types and/or X-ray exposure conditions with a set of bar codes identifying each exam type and exposure condition. As shown in more detail in FIG. 3, chart 68 has a list of X-ray exam types, such as, chest P/A Posterior/Anterior>; chest A/P Anterior/Posterior>; head; limb; abdomen, etc. Each X-ray exam type has a unique identifying bar code, 70A, 70B, 70C, 70D, 70E, etc.

Figure 5:
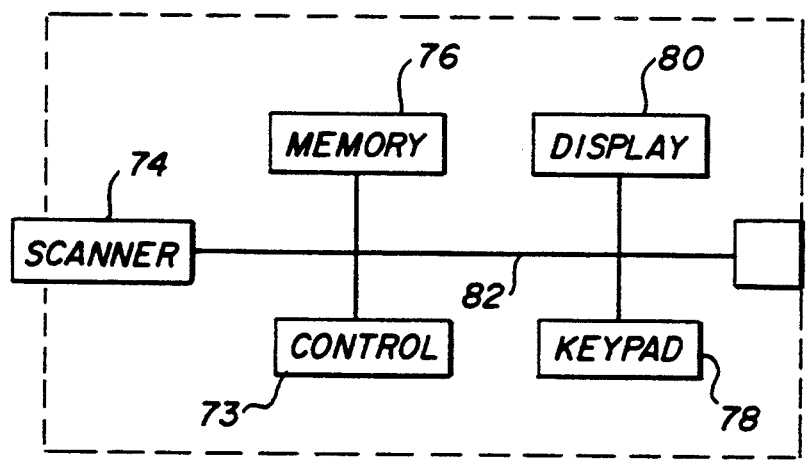
FIG. 5 is a block diagram of the bar code scanner of FIG. 1.

According to the technique of the present invention, an X-ray technician who is responsible for taking X-rays at the medical care facility is provided with a portable bar code scanner 72. Bar code scanner 72 <see FIG. 5) has a laser scanner 74 for scanning bar codes and converting the scanned bar code into an electrical signal which is stored in memory 76. Preferably, scanner 72 has a keyboard 78 for entering data which is stored in memory 76 and also has a display 80 for displaying the input data and other information. Control circuit 73, scanner 74, memory 76, display 80 and keypad 78 are internally connected by bus 82.

At the time a patient is exposed to an X-ray, a technician scans the patient identifying bar code, scans the storage phosphor identifying bar code and scans the bar code identifying the X-ray exam type. Thus, for example, as shown in FIG. 1, X-ray source 28 is positioned over patient 24 and storage phosphor cassette 42 is positioned under the chest area of patient 24. At the time of taking an X-ray, the technician uses bar code scanner 72 to scan patient identifying bar code 66 on patient chart 58, to scan storage phosphor identifying bar code 50 on storage phosphor cassette 42, and to scan X-ray examination type bar code 70A on exam type chart 68. Bar code 70A identifies the X-ray exam type as a chest Anterior to Posterior exam. Chart 68 may also contain other information relating to the X-ray examination, such as, X-ray exposure conditions, patient position, etc., which are also scanned by bar code scanner 72 and stored in memory 76. A technician identifying bar code may also be read. The technician can correct or manually enter data via keypad 78 at the time an X-ray exam is effected.

After the technician has finished an X-ray exam of patient 24, he can move X-ray unit 26 to the bedside of patients 18, 20, and 22 to produce X-ray images in storage phosphor cassettes 36, 38, and 40.

Figure 6:
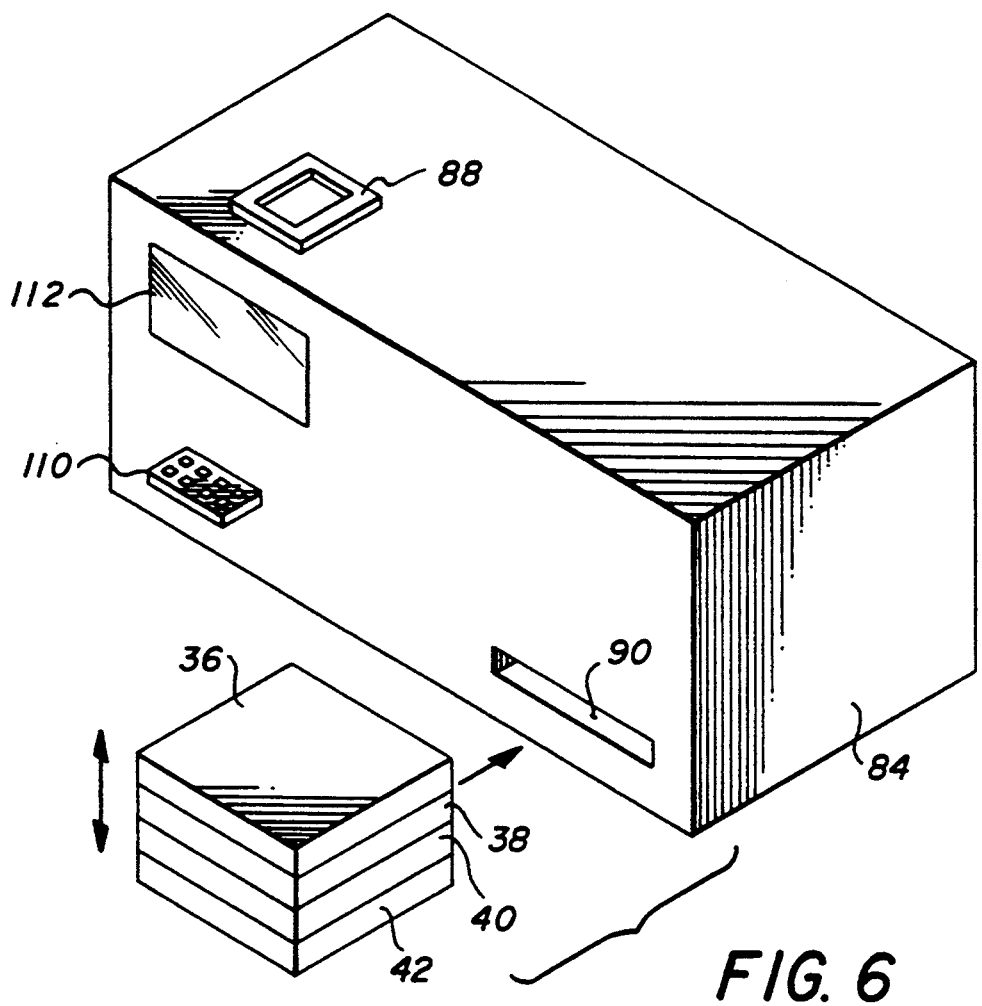
FIG. 6 is a perspective view of a computed radiography storage phosphor reader for reading storage phosphors used in the system of the present invention.

After a set of X-ray exposures have been taken and relevant data for each exposure scanned and stored in memory 76 of portable bar code scanner 72, the technician carries the storage phosphor cassettes 36, 38, 40, and 42 in a stack to a computed radiography storage phosphor reader station. Such a station is shown in FIG. 6 and includes a computed radiography storage phosphor reader 84. Reader 84 has a bar code scanner download station 88. Preferably, a storage phosphor or cassette stacker (not shown) is provided adjacent to reader 84 to sequentially feed exposed storage phosphors into slot 90 of reader 84. The exposed storage phosphor is read by reader 84 and converted to an X-ray image signal which is stored in a suitable memory. At the same time, the technician inserts bar code scanner 72 into download station 88 where information relating to patient identification, storage phosphor identification, X-ray exam type, and other information relating to a specific X-ray exam is downloaded into memory associated with reader 84. As each storage phosphor is inserted into reader 84, and the stored X-ray image is converted into an X-ray image signal, the storage phosphor identifying bar code is read by a bar code reader in storage phosphor reader 84. Thus, the X-ray image signal read from a storage phosphor will be matched with the proper patient, X-ray exam type and other related information for further processing in workstation 86.

Figure 7:
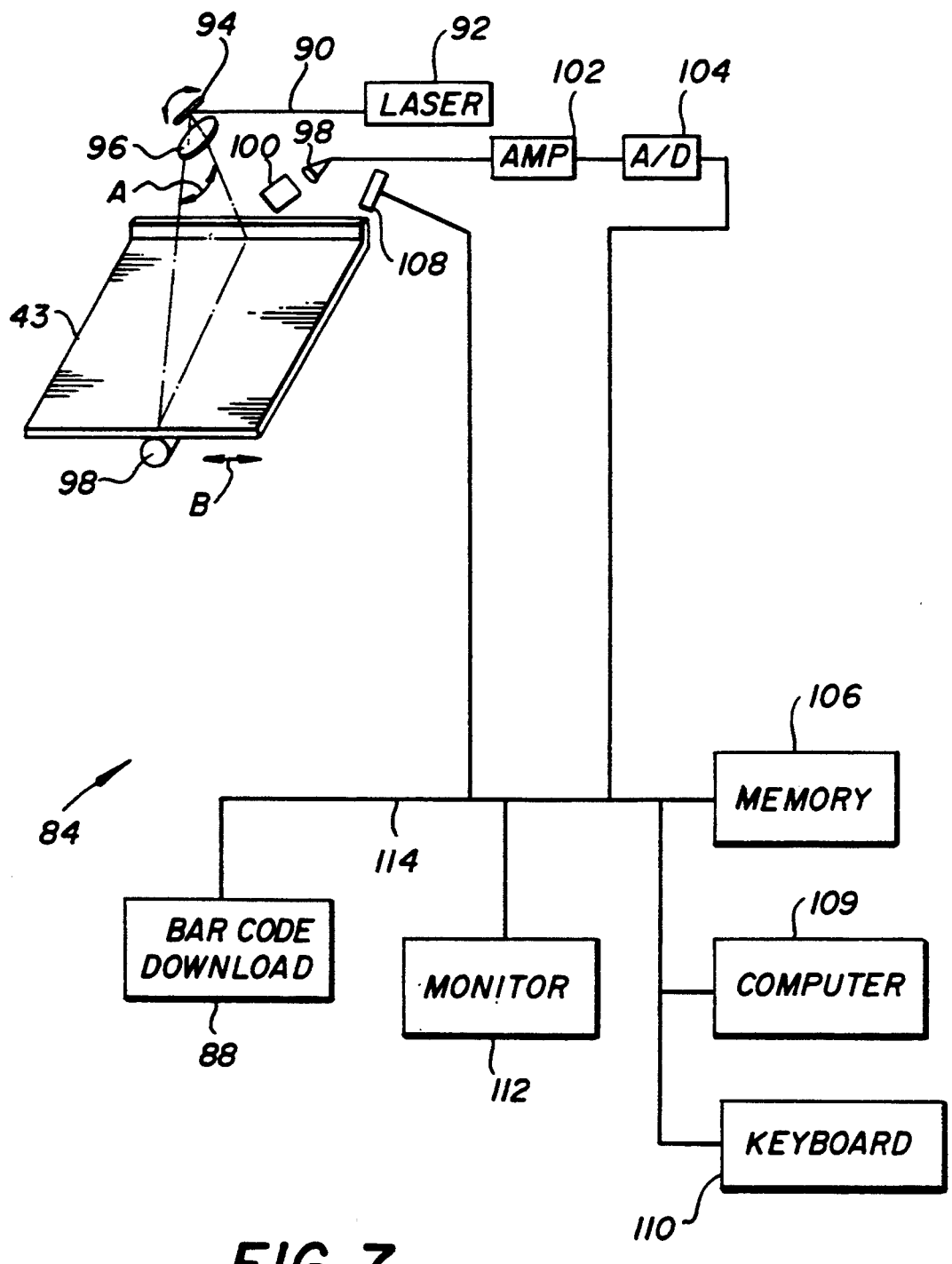
FIG. 7 is a partial block diagram, partial diagrammatic view of the storage phosphor reader shown in FIG. 6.

Referring now to FIG. 7, there is shown in more detail, storage phosphor reader 84. An exposed storage phosphor, such as 43, is removed from its cassette, such as 42, by a plate extraction mechanism <not shown>. Plate 43 stores a latent X-ray image of a patient. A beam 90 of stimulating radiation is generated by laser source 92. A deflector 94, such as a galvo mirror or polygon scanner, scans beam 90 <which has been focused by appropriate optics 96>point by point across storage phosphor 43 in the direction of arrow A. A translation mechanism 98 moves storage phosphor 43 in a direction <indicated by arrow B>perpendicular to the travel of the deflected beam 90, effecting a raster scan of the storage phosphor 43.

The intensity of the stimulated fluorescence is detected by an electrooptic converter which is sensitive at the wavelength of the light emitted by storage phosphor 43. The converter may, for example, be a photomultiplier tube 98 or other photodetector which receives emitted light through an optical filter 100. Filter 100 blocks the stimulating light from laser 92 but passes the emitted light from storage phosphor 43. The signal from photoconverter 98 is amplified and filtered by amplifier 102 and converted to a digital signal by analog-to-digital converter (A/D) 104. The digital signal is stored in memory 106 which also receives the information downloaded from bar code scanner 72 by means of bar code download station 88.

A separate bar code scanner 108 in reader 84 scans the storage phosphor identifying bar code 50 on storage phosphor 43 to identify the X-ray image signal. Reader 84 includes memory 106, a microprocessor 109, keyboard 110, and high resolution monitor 112 connected by bus 114. The patient identification and X-ray exam type (and related) information which have been downloaded from the bar code scanner, are matched by computer 109 to the X-ray image signal which has been read from storage phosphor 43. This information is stored in memory 106. The X-ray image signal is displayed on monitor 112 along with other information relating to the patient, X-ray exam, etc. Keyboard 110 is used to input data and to control reader 84.

Although the invention has been described with reference to preferred embodiments there, it will be understood that variations and modifications can be effected with the spirit and scope of the invention as described above as defined in the appended claims.

What is claimed is:

1. A computed radiography patient identifying system comprising:

patient identifying bar code means adapted to be located with a patient for identifying a patient;

storage phosphor means for storing an x-ray image of a patient, said storage phosphor means having storage phosphor identifying bar code means for identifying the storage phosphor means;

x-ray examination type bar code means locatable with an x-ray source for identifying x-ray examination type characteristics of said x-ray image stored in said storage phosphor means, wherein said x-ray examination type bar code means includes a first set of bar codes identifying unique body parts of a patient and a second set of bar codes identifying x-ray exposure conditions;

hand-held bar code scanner means, having memory, for scanning said patient identifying bar code means, said storage phosphor bar code identifying means, and a bar code from each of the respective first and second sets of said x-ray examination type bar code means at the time said storage phosphor means is exposed to an x-ray image of a patient, to produce patient identifying information, storage phosphor means identifying information, and x-ray examination type information which is stored in said memory;

storage phosphor reader means for converting a stored x-ray image in said storage phosphor means into an x-ray image signal, said storage phosphor reader means having first means for receiving information identifying said storage phosphor means from said storage phosphor bar code identifying means; and second means for receiving from said hand-held bar code scanner means the stored information relating to patient identification, storage phosphor means identification, and x-ray examination type and for matching the received information with said x-ray image signal converted from said storage phosphor means.

2. The system of claim 1, wherein said first receiving means includes a bar code scanner for scanning said bar code of a storage phosphor means read by said reader means.

3. The system of claim 1 wherein said storage phosphor reader means includes a housing, translation means within said housing for translating a storage phosphor means past an image converting position, image converting means at said image converting position for converting a stored x-ray image in a translated storage phosphor means into said x-ray image signal, wherein said first receiving means includes a bar code scanner mounted within said housing for reading said storage phosphor identifying bar code means, and wherein said second receiving means includes a bar code scanner station on the outside of said reader housing for receiving said hand-held bar code scanner means.

4. A computed radiography patient identifying method comprising:

producing a stored x-ray image of a patient in a storage phosphor;

providing unique bar code identifying means for identifying, respectively, said patient, said storage phosphor and the particular body part and particular x-ray exposure conditions for producing said x-ray image from respective sets of body parts and x-ray exposure conditions;

at the time of producing said x-ray image in said storage phosphor, using a hand-held bar code scanner having memory to scan said patient bar code identifying means, said storage phosphor bar code identifying means, and said body part and x-ray exposure conditions bar code identifying means, to produce patient identifying information, storage phosphor identifying information, and body part and x-ray exposure conditions identifying information which is stored in said memory;

reading said stored x-ray image in said storage phosphor and converting it to an x-ray image signal and reading said storage phosphor bar code identifying means to produce a storage phosphor identifying signal matched with said x-ray image signal; and contemporaneously with said reading of said storage phosphor, reading from said hand-held bar code scanner said storage phosphor identifying information, said patient identifying information and said x-ray image producing conditions information, and matching said information with said x-ray image signal from said storage phosphor.

5. A computer radiography patient identifying system comprising:

first and second patient identifying bar code means for identifying first and second patients;

first and second storage phosphor means for storing an x-ray image of a patient, said first and second storage phosphor means having respective first and second storage phosphor bar code identifying means for identifying the respective first and second storage phosphor means;

a mobile x-ray source having associated therewith first and second sets of x-ray examination type bar code identifying means for identifying first and second different examination types;

a hand-held bar code scanner means, having memory, which (1) at the time said mobile x-ray source is used to produce an x-ray image of a first patient in said first storage phosphor means, to scan said first storage phosphor bar code identifying means, said first patient bar code identifying means, and a selected one of each of said first and second sets of examination type bar code identifying means to produce information identifying said first patient, said first storage phosphor means and said selected one of said first and second examination types, and for storing said information in said memory, and (2) at the time said mobile x-ray source is used to produce an x-ray image of a second patient in said second storage phosphor means to scan said second storage phosphor bar code identifying means, said second patient bar code identifying means, and a selected one of each of said first and second sets of examination type bar code identifying means to produce information identifying said second patient, said second storage phosphor means, and said selected ones of said first and second examination types, and for storing said information in said memory;

storage phosphor reader means for sequentially converting a stored x-ray image in said first storage phosphor means into a first x-ray image signal and a stored x-ray image in said second storage phosphor means into a second x-ray image signal, said storage phosphor reader means having means for reading said first and second storage phosphor bar code identifying means to produce identifying information for each of said first and second x-ray image signals; and means for receiving, at the time said first and second storage phosphor means are read, from said handheld bar code scanner memory, said information relating to the first patient identification, the first storage phosphor identification and the first x-ray examination type, and information relating to the second patient identification, the second storage phosphor identification and the second x-ray examination type and for matching said received information with the respective first and second x-ray image signals.

* * * * *